US008431600B2

(12) United States Patent
Dunkel et al.

(10) Patent No.: US 8,431,600 B2
(45) Date of Patent: Apr. 30, 2013

(54) CARBOXAMIDES

(75) Inventors: Ralf Dunkel, Lyons (FR); Hans-Ludwig Elbe, Wuppertal (DE); Herbert Gayer, Monheim (DE); Jörg Nico Greul, Leichlingen (DE); Ulrike Wachendorff-Neumann, Neuwied (DE); Peter Dahmen, Neuss (DE); Ingo Wetcholowsky, Langenfeld (DE); Haruko Sawada, Yuki (JP); Hiroyuki Hadano, Tochigi (JP)

(73) Assignee: Bayer CropScience AG, Monheim (DE)

( * ) Notice: Subject to any disclaimer, the term of this patent is extended or adjusted under 35 U.S.C. 154(b) by 740 days.

(21) Appl. No.: 11/916,436

(22) PCT Filed: May 26, 2006

(86) PCT No.: PCT/EP2006/005070
§ 371 (c)(1),
(2), (4) Date: Nov. 7, 2008

(87) PCT Pub. No.: WO2006/131221
PCT Pub. Date: Dec. 14, 2006

(65) Prior Publication Data
US 2009/0105311 A1    Apr. 23, 2009

(30) Foreign Application Priority Data
Jun. 7, 2005 (DE) .................. 10 2005 025 989

(51) Int. Cl.
*A01N 43/40* (2006.01)
*A01N 43/56* (2006.01)
*A01N 43/78* (2006.01)
*A01N 43/828* (2006.01)
*A01N 37/18* (2006.01)

(52) U.S. Cl.
USPC ........... 514/355; 514/406; 514/617; 514/365; 514/361

(58) Field of Classification Search .............. 514/255.05
See application file for complete search history.

(56) References Cited

U.S. PATENT DOCUMENTS

| 5,914,344 A * | 6/1999 | Yoshikawa et al. ........... 514/406 |
| 7,329,633 B2 * | 2/2008 | Dunkel et al. ................. 504/280 |
| 7,358,214 B2 * | 4/2008 | Dunkel et al. ................. 504/280 |
| 7,521,397 B2 * | 4/2009 | Dunkel et al. ................. 504/280 |
| 7,538,073 B2 * | 5/2009 | Elbe et al. ...................... 504/280 |
| 7,799,739 B2 * | 9/2010 | Dunkel et al. ................. 504/280 |
| 7,820,708 B2 * | 10/2010 | Dunkel et al. ................. 514/406 |
| 7,879,760 B2 * | 2/2011 | Dunkel et al. ................. 504/280 |
| 2006/0116414 A1 * | 6/2006 | Dunkel et al. ................. 514/406 |
| 2007/0004921 A1 * | 1/2007 | Dunkel et al. ................. 546/281.4 |
| 2007/0060579 A1 * | 3/2007 | Wachendorff-Neumann et al. .......... 514/229.2 |
| 2007/0196406 A1 * | 8/2007 | Dunkel et al. ................. 424/405 |
| 2008/0108686 A1 * | 5/2008 | Gewehr et al. ................. 514/406 |
| 2008/0255071 A1 * | 10/2008 | Suty-Heinze et al. ........ 514/147 |
| 2009/0069398 A1 * | 3/2009 | Dunkel et al. ................. 514/406 |
| 2009/0118346 A1 * | 5/2009 | Dunkel et al. ................. 514/406 |
| 2009/0286681 A1 * | 11/2009 | Dahmen et al. ................ 504/100 |

FOREIGN PATENT DOCUMENTS

| WO | WO2005/042492 | * | 5/2005 |
| WO | WO2005/074686 | * | 8/2005 |
| WO | WO2005/123690 | * | 12/2005 |
| WO | WO2006/037632 | * | 4/2006 |

OTHER PUBLICATIONS

Iowa State Fungicide presentation (http://www.extension.iastate.edu/NR/rdonlyres/7411E275-706F-4DEF-A131-BC1610BF827D/5213/ . . . , available May 11, 2004).*
FRAC code list 2009 (http://www.frac.infograc/publication/anhang/frac_code_list.pdf).*
D.S. Mueller et al, "Efficacy of Fungicides on *Sclerotinia sclerotiorum* and Their Potential for Control of *Sclerotinia* stem Rot on Soybean" in Plant Disease, 86, 26•31 (2002).
M.R. Miles, "International Fungicide Efficacy Trials for the Management of Soybean Rust" in Plant Disease, 91, 1450•1458 (2007).
T.A. Mueller et al, "Effect of Fungicide and Timing of Application on Soybean Rust Severity and Yield" in Plant Disease, 93, 243•248 (2009).
M.C. Meyer et al, "Fungicides Efficacy for Control Asian Soybean Rust and Rhizoctonia Aerial Blight in the Northeastern Brazil" in Proceedings of 2007 National Soybean Rust Symposium (Dec. 12•14, 2007; Louisville, Kentucky).
J. Gaska, "To Treat or Not to Treat? Fungicide Seed Treatments for Soybean," pamphlet of University of Wisconsin Division of Cooperative Extension Division of Cooperative Extension (2004).
Claudia V. Godoy, "Eficiencia de fungicidas para o controle da ferrugem asiática da soja, *Phakopsora pachyrhizi*, na safra Oct. 2009: resultados sumarizados dos ensaios cooperativos" in Circular Tecnica, 80 (Aug. 2010) [only in Portuguese but article describes efficacy of fungicides for the control of asiatic rust in soybeans].
Jankovics et al.; "Peach Rusty Spot Is Caused by the Apple Powdery Mildew Fungus, *Podosphaera leucotricha*"; Plant Disease; Jun. 2011; vol. 95; pp. 719-724; The American Phytopathological Society.
Turechek et al.; "Powdery Mildew of Apple"; *Podosphaera leucotricha*; Integrated Pest Management; Tree Fruit; 2004; www.nysipm.cornell.edu/factsheets/treefruit/diseases/pm/apple_pm.pdf; Cornell University and the New York State IPM Program.

* cited by examiner

*Primary Examiner* — Mina Haghighatian
*Assistant Examiner* — Erin Hirt
(74) *Attorney, Agent, or Firm* — Baker Donelson Bearman Caldwell & Berkowitz, PC

(57) ABSTRACT

Use of carboxamides of the formula (I)

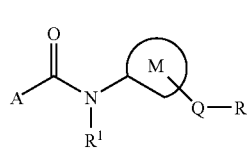

(I)

in which
A, $R^1$, M, Q and R are as defined in the description
for controlling certain rust fungi, such as soya bean rust and coffee rust, in crop protection.

4 Claims, No Drawings

CARBOXAMIDES

CROSS REFERECE TO RELATED APPLICATIONS

This is a §371 National Stage Application of International Application No. PCT/EP2006/005070 filed May 26, 2006, which claims priority to DE 102005025989.8 filed Jun. 7, 2005.

BACKGROUND OF THE INVENTION

1. Field of the Invention
2. Description of Related Art

The present invention relates to known carboxamides and to their use for controlling unwanted microorganisms.

It is already known that numerous carboxamides have fungicidal properties (cf., for example, WO 04/103975, WO 04/103953, WO 03/070705, WO 03/010149, WO 02/059086, EP-A 0 824 099, EP-A 0 737 682, EP-A 0 591 699, EP-A 0 589 301, EP-A 0 545 099, DE-A 24 09 011, DE-A 20 06 472, JP-A 2001-302605, JP-A 10-251240, JP-A 8-176112, JP-A 8-92223 and JP-A 53-72823). Thus, for example, numerous carboxamides and their use against *Puccinia* species, such as, for example, *Puccinia recondita*, or *Uromyces* species, such as, for example, *Uromyces appendiculatus*, are known. The activity of these compounds is good; however, in some cases, for example at low application rates, it is unsatisfactory. It has now been found that these carboxamides are also effective against other rust species, such as, for example, soya bean rust, which has only recently been encountered, *Phakopsora* species, such as, for example, *Phakopsora sojae*, *Phakopsora pachyrhizi*, *Phakopsora vignae*, *Uredo sojae*, *Uromyces sojae*, but also against other rust species, such as, for example, coffee rust, *Helileia vastarix*.

SUMMARY OF THE INVENTION

It has now been found that the carboxamides of the formula (I)

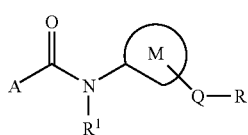

in which

A represents optionally substituted aryl or an aromatic or non-aromatic 5- or 6-membered carbocyclic or heterocyclic ring having 1 to 3 heteroatoms, which may be O, N or S, where the carbo- or heterocycle may carry 1, 2 or 3 substituents selected from the group consisting of alkyl, halogen, haloalkyl, alkylthio, alkylsulphinyl and alkylsulphonyl, $R^1$ represents hydrogen, $C_1$-$C_8$-alkyl, $C_1$-$C_6$-alkylsulphinyl, $C_1$-$C_6$-alkylsulphonyl, $C_1$-$C_4$-alkoxy$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_8$-alkyl)carbonyl, ($C_1$-$C_8$-alkoxy)carbonyl, ($C_1$-$C_8$-alkylthio)carbonyl, ($C_1$-$C_4$-alkoxy-$C_1$-$C_4$-alkyl)carbonyl, ($C_3$-$C_6$-alkenyloxy)carbonyl, ($C_3$-$C_6$-alkinyloxy)carbonyl, ($C_3$-$C_8$-cycloalkyl)carbonyl; ($C_1$-$C_6$-haloalkyl)carbonyl, ($C_1$-$C_6$-haloalkoxy)carbonyl, ($C_1$-$C_6$-haloalkylthio)carbonyl, (halo-$C_1$-$C_4$-alkoxy-$C_1$-$C_4$-alkyl)carbonyl, ($C_3$-$C_6$-haloalkenyloxy)carbonyl, ($C_3$-$C_6$-haloalkinyloxy)carbonyl, ($C_3$-$C_8$-halocycloalkyl)carbonyl having in each case 1 to 9 fluorine, chlorine and/or bromine atoms; or
—$CH_2$—$C\!\equiv\!C$—$R^{1-A}$, —$CH_2$—$CH\!=\!CH$—$R^{1-A}$, —$CH\!=\!C\!=\!CH$—$R^{1-A}$, —$C(\!=\!O)C(\!=\!O)R^2$, —$CONR^3R^4$ or —$CH_2NR^5R^6$, $R^{1-A}$ represents hydrogen, $C_1$-$C_6$-alkyl, $C_1$-$C_6$-haloalkyl, $C_2$-$C_6$-alkenyl, $C_2$-$C_6$-alkinyl, $C_3$-$C_7$-cycloalkyl, ($C_1$-$C_4$-alkoxy)carbonyl, ($C_3$-$C_6$-alkenyloxy)carbonyl, ($C_3$-$C_6$-alkinyloxy)carbonyl or cyano, $R^2$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^3$ and $R^4$ independently of one another each represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^3$ and $R^4$ furthermore together with the nitrogen atom to which they are attached form a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulphur and $NR^7$, $R^5$ and $R^6$ independently of one another represent hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms, $R^5$ and $R^6$ furthermore together with the nitrogen atom to which they are attached represent a saturated heterocycle which is optionally mono- or polysubstituted by identical or different substituents from the group consisting of halogen and $C_1$-$C_4$-alkyl and which has 5 to 8 ring atoms, where the heterocycle may contain 1 or 2 further non-adjacent heteroatoms from the group consisting of oxygen, sulphur and $NR^7$, $R^7$ represents hydrogen or $C_1$-$C_6$-alkyl, M represents a phenyl or thiophene ring, each of which is monosubstituted by $R^8$, or represents substituted $C_3$-$C_6$-cycloalkyl or $C_3$-$C_6$-cycloalkenyl, each of which is mono- to tetrasubstituted by $R^{8-B}$, $R^8$ represents hydrogen, fluorine, chlorine, methyl, isopropyl, methylthio or trifluoromethyl, $R^{8-B}$ represents hydrogen, fluorine, chlorine, $C_1$-$C_4$-alkyl or $C_1$-$C_4$-haloalkyl, Q represents a direct bond, $C_1$-$C_4$-alkylene, $C_2$-$C_4$-alkenylene, O, S, SO, $SO_2$ or $NR^9$, $R^9$ represents hydrogen, $C_1$-$C_8$-alkyl, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkinyl, $C_1$-$C_6$-haloalkyl, $C_2$-$C_6$-haloalkenyl, $C_2$-$C_6$-haloalkinyl or $C_3$-$C_6$-cycloalkyl, R represents in each case optionally substituted phenyl, cycloalkyl or bicycloalkyl; or represents unsubstituted $C_2$-$C_{20}$-alkyl or represents optionally substituted $C_1$-$C_{20}$-alkyl, can be used for controlling certain rust fungi, such as soya bean rust and coffee rust, in crop protection.

The compounds of the formula (I) are known.

DETAILED DESCRIPTION OF A PREFERRED EMBODIMENT

If appropriate, the carboxamides of the formula (I) can be present as mixtures of various possible isomeric forms, in particular stereoisomers, such as, for example, E and Z, threo and erythro, and also optical isomers, and, if appropriate, also of tautomers. The formula (I) includes both the E and the Z isomers, and the threo and erythro and also the optical isomers, any mixtures of these isomers and the possible tautomeric forms.

The formula (I) provides a general definition of the carboxamides which can be used according to the invention. Preferred radical definitions are given below.

A preferably represents one of the radicals A1 to A19 below

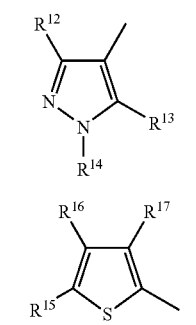

A1

A2

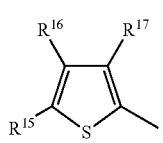

A3

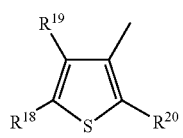

A4

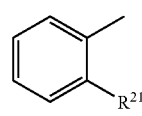

A5

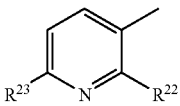

A6

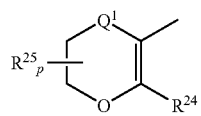

A7

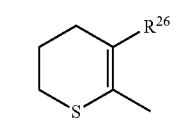

A8

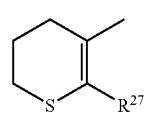

-continued

A9

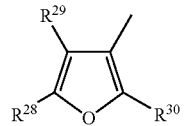

A10

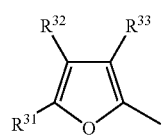

A11

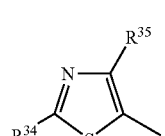

A12

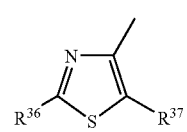

A13

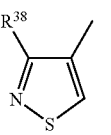

A14

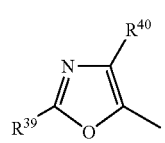

A15

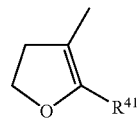

A16

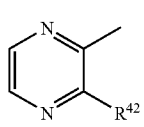

A17

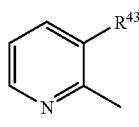

A18

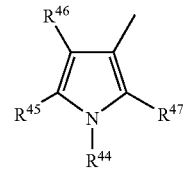

A19 in which $R^{12}$ represents hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$- haloalkyl, $C_1$-$C_4$-haloalkoxy or $C_1$-$C_4$-haloalkylthio having in each case 1 to 5 halogen atoms, aminocarbonyl or aminocarbonyl-$C_1$-$C_4$-alkyl, $R^{13}$ represents hydrogen, halogen, cyano, $C_1$-$C_4$-alkyl, $C_1$-$C_4$-alkoxy or $C_1$-$C_4$-alkylthio, $R^{14}$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkyl, $C_1$-$C_4$-haloalkoxy-$C_1$-$C_4$-alkyl having in each case 1 to 5 halogen atoms, or phenyl, $R^{15}$ and $R^{16}$ independently of one another represent hydrogen, halogen, $C_1$-$C_4$-alkyl or $C_1$-$C_4$-haloalkyl having 1 to 5 halogen atoms, $R^{17}$ represents halogen, cyano or $C_1$-$C_4$-alkyl, or $C_1$-$C_4$-haloalkyl or $C_1$-$C_4$-haloalkoxy having in each case 1 to 5 halogen atoms, $R^{18}$ and $R^{19}$ independently of one another represent hydrogen, halogen, $C_1$-$C_4$-alkyl or $C_1$-$C_4$-haloalkyl having 1 to 5 halogen atoms, $R^{20}$ represents hydrogen, halogen, $C_1$-$C_4$-alkyl or $C_1$-$C_4$-haloalkyl having 1 to 5 halogen atoms, $R^{21}$ represents hydrogen, halogen, hydroxyl, cyano, $C_1$-$C_6$-alkyl, $C_1$-$C_4$-haloalkyl, $C_1$-$C_4$-haloalkoxy or $C_1$-$C_4$-haloalkylthio having in each case 1 to 5 halogen atoms, $R^{22}$ represents halogen, hydroxyl, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms, $R^{23}$ represents hydrogen, halogen, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy having in each case 1 to 5 halogen atoms, $C_1$-$C_4$-alkylsulphinyl or $C_1$-$C_4$-alkylsulphonyl, $R^{24}$ represents $C_1$-$C_4$-alkyl or $C_1$-$C_4$-haloalkyl having 1 to 5 halogen atoms, $R^{25}$ represents $C_1$-$C_4$-alkyl, $Q^1$ represents S (sulphur), SO, $SO_2$ or $CH_2$, p represents 0, 1 or 2, where $R^{25}$ represents identical or different radicals if p represents 2, $R^{26}$ represents $C_1$-$C_4$-alkyl or $C_1$-$C_4$-haloalkyl having 1 to 5 halogen atoms, $R^{27}$ represents $C_1$-$C_4$-alkyl or $C_1$-$C_4$-haloalkyl having 1 to 5 halogen atoms, $R^{28}$ and $R^{29}$ independently of one another represent hydrogen, halogen, amino, $C_1$-$C_4$-alkyl or $C_1$-$C_4$-haloalkyl having 1 to 5 halogen atoms, $R^{30}$ represents hydrogen, halogen, $C_1$-$C_4$-alkyl or $C_1$-$C_4$-haloalkyl having 1 to 5 halogen atoms, $R^{31}$ and $R^{32}$ independently of one another represent hydrogen, halogen, amino, nitro, $C_1$-$C_4$-alkyl or $C_1$-$C_4$-haloalkyl having 1 to 5 halogen atoms, $R^{33}$ represents hydrogen, halogen, $C_1$-$C_4$-alkyl or $C_1$-$C_4$-haloalkyl having 1 to 5 halogen atoms, $R^{34}$ represents hydrogen, halogen, amino, $C_1$-$C_4$-alkylamino, di($C_1$-$C_4$-alkyl)amino, cyano, $C_1$-$C_4$-alkyl or $C_1$-$C_4$-haloalkyl having 1 to 5 halogen atoms, $R^{35}$ represents halogen, $C_1$-$C_4$-alkyl or $C_1$-$C_4$-haloalkyl having 1 to 5 halogen atoms, $R^{36}$ represents hydrogen, halogen, amino, $C_1$-$C_4$-alkylamino, di($C_1$-$C_4$-alkyl)amino, cyano, $C_1$-$C_4$-alkyl or $C_1$-$C_4$-haloalkyl having 1 to 5 halogen atoms, $R^{37}$ represents halogen, $C_1$-$C_4$-alkyl or $C_1$-$C_4$-haloalkyl having 1 to 5 halogen atoms, $R^{38}$ represents halogen, $C_1$-$C_4$-alkyl or $C_1$-$C_4$-haloalkyl having 1 to 5 halogen atoms, $R^{39}$ represents hydrogen or $C_1$-$C_4$-alkyl, $R^{40}$ represents halogen or $C_1$-$C_4$-alkyl, $R^{41}$ represents $C_1$-$C_4$-alkyl or $C_1$-$C_4$-haloalkyl having 1 to 5 halogen atoms, $R^{42}$ represents hydrogen, halogen, $C_1$-$C_4$-alkyl or $C_1$-$C_4$-haloalkyl having 1 to 5 halogen atoms, $R^{43}$ represents halogen, hydroxyl, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms, $R^{44}$ represents hydrogen, cyano, $C_1$-$C_4$-alkyl, $C_1$-$C_4$-haloalkyl having 1 to 5 halogen atoms, $C_1$-$C_4$-alkoxy-$C_1$-$C_4$-alkyl, hydroxy-$C_1$-$C_4$-alkyl, $C_1$-$C_4$-alkylsulphonyl, di($C_1$-$C_4$-alkyl)aminosulphonyl, $C_1$-$C_6$-alkylcarbonyl or in each case optionally substituted phenylsulphonyl or benzoyl, $R^{45}$ represents hydrogen, halogen, $C_1$-$C_4$-alkyl or $C_1$-$C_4$-haloalkyl having 1 to 5 halogen atoms, $R^{46}$ represents hydrogen, halogen, cyano, $C_1$-$C_4$-alkyl or $C_1$-$C_4$-haloalkyl having 1 to 5 halogen atoms, $R^{47}$ represents hydrogen, halogen, $C_1$-$C_4$-alkyl or $C_1$-$C_4$-haloalkyl having 1 to 5 halogen atoms, $R^{48}$ represents $C_1$-$C_4$-alkyl.

A particularly preferably represents one of the radicals A1, A2, A3, A4, A5, A6, A9, A10, A11, A12, A17 or A18.

A very particularly preferably represents one of the radicals A1, A2, A4, A5, A6, A9, A11, A16, A17, A18.

A especially preferably represents the radical A1.

A furthermore especially preferably represents the radical A2.

A furthermore especially preferably represents the radical A4.

A furthermore especially preferably represents the radical A5.

A furthermore especially preferably represents the radical A6.

A furthermore especially preferably represents the radical A9.

A furthermore especially preferably represents the radical A11.

A furthermore especially preferably represents the radical A16.

A furthermore especially preferably represents the radical A18.

$R^1$ preferably represents hydrogen, $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_6$-alkyl)carbonyl, ($C_1$-$C_4$-alkoxy)carbonyl, ($C_1$-$C_4$-alkylthio)carbonyl, ($C_1$-$C_3$-alkoxy-$C_1$-$C_3$-alkyl)carbonyl, ($C_3$-$C_4$-alkenyloxy)carbonyl, ($C_3$-$C_4$-alkinyloxy)carbonyl, ($C_3$-$C_6$-cycloalkyl)carbonyl; ($C_1$-$C_4$-haloalkyl)carbonyl, ($C_1$-$C_4$-haloalkoxy)carbonyl, ($C_1$-$C_4$-haloalkylthio)carbonyl, (halo-$C_1$-$C_3$-alkoxy-$C_1$-$C_3$-alkyl)carbonyl, ($C_3$-$C_4$-haloalkenyloxy)carbonyl, ($C_3$-$C_4$-haloalkinyloxy)carbonyl, ($C_3$-$C_6$-halocycloalkyl)carbonyl having in each case 1 to 9 fluorine, chlorine and/or bromine atoms; or —$CH_2$—C≡C—$R^{1-A}$, —$CH_2$—CH=CH—$R^{1-A}$, —CH=C=CH—$R^{1-A}$, —C(=O)C(=O)$R^2$, —$CONR^3R^4$ or —$CH_2NR^5R^6$.

$R^1$ particularly preferably represents hydrogen, methyl, ethyl, n- or isopropyl, n-, iso-, sec- or tert-butyl, pentyl or hexyl, methylsulphinyl, ethylsulphinyl, n- or isopropylsulphinyl, n-, iso-, sec- or tert-butylsulphinyl, methylsulphonyl, ethylsulphonyl, n- or isopropylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl; formyl, —$CH_2$—CHO, —$(CH_2)_2$—CHO, —$CH_2$—CO—$CH_3$, —$CH_2$—CO—$CH_2CH_3$, —$CH_2$—CO—CH$(CH_3)_2$, —$(CH_2)_2$—CO—$CH_3$, —$(CH_2)_2$—CO—$CH_2CH_3$, —$(CH_2)_2$—CO—CH$(CH_3)_2$, —$CH_2$—$CO_2CH_3$, —$CH_2$—$CO_2CH_2CH_3$, —$CH_2$—$CO_2$CH$(CH_3)_2$, —$(CH_2)_2$—$CO_2CH_3$, —$(CH_2)_2$—$CO_2CH_2CH_3$, —$(CH_2)_2$—$CO_2$CH$(CH_3)_2$, —$CH_2$—CO—$CF_3$, —$CH_2$—CO—$CCl_3$, —$CH_2$—CO—$CH_2CF_3$, —$CH_2$—CO—$CH_2CCl_3$, —$(CH_2)_2$—CO—$CH_2CF_3$, —$(CH_2)_2$—CO—$CH_2CCl_3$, —$CH_2$—$CO_2CH_2CF_3$, —$CH_2$—$CO_2CF_2CF_3$, —$CH_2$—$CO_2CH_2CCl_3$, —$CH_2$—$CO_2CCl_2CCl_3$, —$(CH_2)_2$—$CO_2CH_2CF_3$, —$(CH_2)_2$—$CO_2CF_2CF_3$, —$(CH_2)_2$—$CO_2CH_2CCl_3$, —$(CH_2)_2$—$CO_2CCl_2CCl_3$;
methylcarbonyl, ethylcarbonyl, n-propylcarbonyl, isopropylcarbonyl, tert-butylcarbonyl, methoxycarbonyl, ethoxycarbonyl, isopropoxycarbonyl, tert-butoxycarbonyl, methylthiocarbonyl, ethylthiocarbonyl, isopropylthiocarbonyl, tert-butylthiocarbonyl, methoxymethylcarbonyl, ethoxymethylcarbonyl, cyclopropylcarbonyl; trifluoromethylcarbonyl, trifluoromethoxycarbonyl, trifluoromethylthiocarbonyl, or —$CH_2$—C≡C—$R^{1-A}$, —$CH_2$—CH=CH—$R^{1-A}$, —CH=C=CH—$R^{1-A}$, —C(=O)C(=O)$R^2$, —CONR$^3$R$^4$ or —$CH_2$NR$^5$R$^6$.

$R^1$ very particularly preferably represents hydrogen, methyl, methoxymethyl, methoxymethylcarbonyl, ethoxymethylcarbonyl, formyl, —$CH_2$—C≡CH, —$CH_2$—CH=$CH_2$, —CH=C=$CH_2$, —$CH_2$—CHO, —$(CH_2)_2$—CHO, —$CH_2$—CO—$CH_3$, —$CH_2$—CO—$CH_2CH_3$, —$CH_2$—CO—CH$(CH_3)_2$, —C(=O)CHO, —C(=O)C(=O)$CH_3$, —C(=O)C(=O)$CH_2OCH_3$, —C(=O)$CO_2CH_3$, —C(=O)$CO_2CH_2CH_3$.

$R^{1-A}$ preferably represents hydrogen, $C_1$-$C_4$-alkyl, $C_1$-$C_4$-haloalkyl, $C_2$-$C_4$-alkenyl, $C_2$-$C_4$-alkinyl, $C_3$-$C_6$-cycloalkyl, ($C_1$-$C_4$-alkoxy)carbonyl or cyano.

$R^{1-A}$ particularly preferably represents hydrogen, methyl or ethyl.

$R^2$ preferably represents hydrogen, $C_1$-$C_6$-alkyl, $C_1$-$C_4$-alkoxy, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkoxy, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^2$ particularly preferably represents hydrogen, methyl, ethyl, n- or isopropyl, tert-butyl, methoxy, ethoxy, n- or isopropoxy, tert-butoxy, methoxymethyl, cyclopropyl; trifluoromethyl, trifluoromethoxy.

$R^3$ and $R^4$ independently of one another preferably represent hydrogen, $C_1$-$C_6$-alkyl, $C_1$-$C_3$-alkoxy-$C_1$-$C_3$-alkyl, $C_3$-$C_6$-cycloalkyl; $C_1$-$C_4$-haloalkyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^3$ and $R^4$ furthermore together with the nitrogen atom to which they are attached preferably form a saturated heterocycle which is optionally mono- to tetrasubstituted by identical or different substituents from the group consisting of halogen and $C_1$-$C_4$-alkyl and which has 5 or 6 ring atoms, where the heterocycle may contain 1 or 2 further non-adjacent heteroatoms from the group consisting of oxygen, sulphur and NR$^7$.

$R^3$ and $R^4$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^3$ and $R^4$ furthermore together with the nitrogen atom to which they are attached particularly preferably form a saturated heterocycle from the group consisting of morpholine, thiomorpholine and piperazine, where the piperazine may be substituted on a second nitrogen atom by $R^7$, each of which radical is optionally mono- to tetrasubstituted by identical or different substituents from the group consisting of fluorine, chlorine, bromine and methyl.

$R^5$ and $R^6$ independently of one another preferably represent hydrogen, $C_1$-$C_6$-alkyl, $C_3$-$C_6$-cycloalkyl; $C_1$-$C_4$-haloalkyl, $C_3$-$C_6$-halocycloalkyl having in each case 1 to 9 fluorine, chlorine and/or bromine atoms.

$R^5$ and $R^6$ furthermore together with the nitrogen atom to which they are attached preferably form a saturated heterocycle which is optionally mono- or polysubstituted by identical or different substituents from the group consisting of halogen and $C_1$-$C_4$-alkyl and which has 5 or 6 ring atoms, where the heterocycle may contain 1 or 2 further non-adjacent heteroatoms from the group consisting of oxygen, sulphur and NR$^7$.

$R^5$ and $R^6$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^5$ and $R^6$ furthermore together with the nitrogen atom to which they are attached particularly preferably form a saturated heterocycle from the group consisting of morpholine, thiomorpholine and piperazine, where the piperazine may be substituted on a second nitrogen atom by $R^7$, each of which radical is optionally mono- to tetrasubstituted by identical or different substituents from the group consisting of fluorine, chlorine, bromine and methyl.

$R^7$ preferably represents hydrogen or $C_1$-$C_4$-alkyl.

$R^7$ particularly preferably represents hydrogen, methyl, ethyl, n- or isopropyl, n-, iso-, sec- or tert-butyl.

M preferably represents one of the cycles below

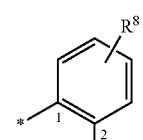

M-1

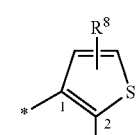

M-7

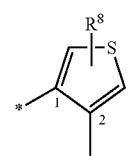

M-8

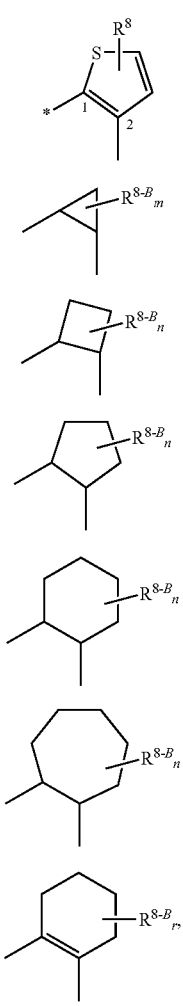

where the bond marked "*" is attached to the amide.

M particularly preferably represents a ring selected from the group consisting of M-1, M-7, M-12, M-14, M-15 or M-17.

M very particularly preferably represents the ring M-1.

M furthermore very particularly preferably represents the ring M-7.

M furthermore particularly preferably represents the ring M-12.

M furthermore very particularly preferably represents the ring M-14.

M furthermore very particularly preferably represents the ring M-15.

M furthermore very particularly preferably represents the ring M-17.

m represents 0, 1 or 2.

n represents 0, 1, 2, 3 or 4.

r represents 0 or 1.

$R^8$ preferably represents hydrogen.

$R^8$, if M represents M-1, furthermore preferably represents fluorine, where fluorine is particularly preferably in the 4-, 5- or 6-position, very particularly preferably in the 4- or 6-position, especially in the 4-position.

$R^8$, if M represents M-1, furthermore preferably represents chlorine, where chlorine is particularly preferably in the 4- or 6-position.

$R^8$, if M represents M-1, furthermore preferably represents methyl, where methyl is particularly preferably in the 3-position.

$R^8$, if M represents M-1, furthermore preferably represents trifluoromethyl, where trifluoromethyl is particularly preferably in the 4- or 6-position.

$R^8$, if M represents M-2, M-3, M-4 or M-5, furthermore preferably represents fluorine, where fluorine is particularly preferably in the 6-position (M-2, M-3) or in the 3-position (M-4, M-5).

$R^8$ if M represents M-2, M-3, M-4 or M-5, furthermore preferably represents chlorine, where chlorine is particularly preferably in the 6-position (M-2, M-3) or in the 3-position (M-4, M-5).

$R^8$, if M represents M-2, M-3, M-4 or M-5, furthermore preferably represents methyl, where methyl is particularly preferably in the 4-position (M-2) or in the 3-position (M-3, M-4, M-5).

$R^8$, if M represents M-6, furthermore preferably represents methyl, where methyl is particularly preferably in the 3-position.

$R^8$, if M represents M-6, furthermore preferably represents trifluoromethyl, where trifluoromethyl is particularly preferably in the 3-position.

$R^8$, if M represents M-7, M-8 or M-9, furthermore preferably represents chlorine, where chlorine is particularly preferably in the 5-position (M-7, M-8) or in the 3-position (M-9).

$R^8$, if M represents M-7, M-8 or M-9, furthermore preferably represents methyl, where methyl is particularly preferably in the 5-position (M-7, M-8) or in the 3-position (M-9).

$R^{8-B}$ preferably represents fluorine, chlorine, methyl, ethyl, n- or isopropyl, n-, iso-, sec- or tert-butyl, trifluoromethyl or difluoromethyl, where the radicals $R^{8-B}$ may be identical or different if m or n is greater than 1.

Q preferably represents a direct bond.

Q furthermore preferably represents —CH$_2$—, —(CH$_2$)$_2$—, —(CH$_2$)$_3$—, —CH(CH$_3$)—, —C(CH$_3$)$_2$—, particularly preferably represents —CH$_2$—, —(CH$_2$)$_2$—, —CH(CH$_3$)—.

Q furthermore preferably represents —CH=CH—, —CH$_2$—CH=CH—, —CH(CH$_3$)—CH=CH—, particularly preferably represents —CH=CH—, —CH$_2$—CH=CH—.

Q furthermore preferably represents O.

Q furthermore preferably represents S.

Q furthermore preferably represents SO.

Q furthermore preferably represents SO$_2$

Q furthermore preferably represents NR$^9$, particularly preferably represents NH.

$R^9$ preferably represents hydrogen, C$_1$-C$_6$-alkyl, C$_1$-C$_3$-alkoxy-C$_1$-C$_3$-alkyl, C$_1$-C$_3$-alkylthioC$_1$-C$_3$-alkyl or C$_3$-C$_6$-cycloalkyl.

$R^9$ particularly preferably represents hydrogen, methyl, ethyl, n- or isopropyl, n-, sec-, iso- or tert-butyl, methoxymethyl, ethoxymethyl, methoxyethyl, ethoxyethyl, methylthiomethyl, ethylthiomethyl, methylthioethyl, ethylthioethyl or cyclopropyl.

$R^9$ very particularly preferably represents hydrogen, methyl, ethyl, n- or isopropyl, iso- or tert-butyl, methoxymethyl or methylthiomethyl.

R preferably represents phenyl which is optionally mono- to pentasubstituted by identical or different substituents, where the substituents are selected from the list $W^1$.

R particularly preferably represents monosubstituted phenyl, where the substituents are selected from the list $W^1$.

R also particularly preferably represents phenyl which is disubstituted by identical or different substituents, where the substituents are selected from the list $W^1$.

R also particularly preferably represents phenyl which is trisubstituted by identical or different substituents, where the substituents are selected from the list $W^1$.

R very particularly preferably represents phenyl which is monosubstituted in the 4-position, where the substituents are selected from the list $W^1$.

R very particularly preferably represents phenyl which is disubstituted by identical or different substituents in the 3,4-position, where the substituents are selected from the list $W^1$.

R very particularly preferably represents phenyl which is disubstituted by identical or different substituents in the 2,4-position, where the substituents are selected from the list $W^1$.

R very particularly preferably represents phenyl which is disubstituted by identical or different substituents in the 3,5-position, where the substituents are selected from the list $W^1$.

R very particularly preferably represents phenyl which is trisubstituted by identical or different substituents in the 2,4,6-position, where the substituents are selected from the list $W^1$.

$W^1$ represents halogen, cyano, nitro, amino, hydroxyl, formyl, carboxyl, carbamoyl, thiocarbamoyl;
in each case straight-chain or branched alkyl, hydroxyalkyl, oxoalkyl, alkoxy, alkoxyalkyl, alkylthioalkyl, dialkoxyalkyl, alkylthio, alkylsulphinyl or alkylsulphonyl having in each case 1 to 8 carbon atoms;
in each case straight-chain or branched alkenyl or alkenyloxy having in each case 2 to 6 carbon atoms;
in each case straight-chain or branched haloalkyl, haloalkoxy, haloalkylthio, haloalkylsulphinyl or haloalkylsulphonyl having in each case 1 to 6 carbon atoms and 1 to 13 identical or different halogen atoms;
in each case straight-chain or branched haloalkenyl or haloalkenyloxy having in each case 2 to 6 carbon atoms and 1 to 11 identical or different halogen atoms;
in each case straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy having 1 to 6 carbon atoms in the respective hydrocarbon chains, alkenylcarbonyl or alkinylcarbonyl having 2 to 6 carbon atoms in the respective hydrocarbon chains;
cycloalkyl or cycloalkyloxy having in each case 3 to 6 carbon atoms;
in each case doubly attached alkylene having 3 or 4 carbon atoms, oxyalkylene having 2 or 3 carbon atoms or dioxyalkylene having 1 or 2 carbon atoms, each of which radical is optionally mono- to tetrasubstituted by identical or different substituents from the group consisting of fluorine, chlorine, oxo, methyl, trifluoromethyl and ethyl;
or a grouping —$C(Q^1)$=N-$Q^2$, in which
$Q^1$ represents hydrogen, hydroxyl, alkyl having 1 to 4 carbon atoms, haloalkyl having 1 to 4 carbon atoms and 1 to 9 identical or different halogen atoms or cycloalkyl having 1 to 6 carbon atoms and
$Q^2$ represents hydroxyl, amino, methylamino, phenyl, benzyl or represents in each case optionally halogen-, cyano-, hydroxyl-, alkoxy-, alkylthio-, alkylamino-, dialkylamino- or phenyl-substituted alkyl or alkoxy having 1 to 4 carbon atoms, or represents alkenyloxy or alkinyloxy having in each case 2 to 4 carbon atoms,
and also phenyl, phenoxy, phenylthio, benzoyl, benzoylethenyl, cinnamoyl, heterocyclyl or phenylalkyl, phenylalkyloxy, phenylalkylthio or heterocyclylalkyl having in each case 1 to 3 carbon atoms in the respective alkyl moieties, each of which radical is optionally mono- to trisubstituted in the cyclic part by halogen and/or straight-chain or branched alkyl or alkoxy having 1 to 4 carbon atoms.

$W^1$ preferably represents fluorine, chlorine, bromine, methyl, ethyl, n- or isopropyl, n-, iso-, sec- or tert-butyl, methoxy, ethoxy, n- or isopropoxy, trifluoromethyl, trifluoroethyl, difluoromethoxy, trifluoromethoxy, difluorochloromethoxy, trifluoroethoxy, in each case doubly attached difluoromethylenedioxy or tetrafluoroethylenedioxy,
or a grouping —$C(Q^1)$=N-$Q^2$, in which
$Q^1$ represents hydrogen, methyl, ethyl, trifluoromethyl or cyclopropyl and
$Q^2$ represents hydroxyl, methoxy, ethoxy, propoxy or isopropoxy.

R furthermore preferably represents cycloalkyl or bicycloalkyl, each of which is optionally mono- to tetrasubstituted by identical or different substituents from the group consisting of $C_1$-$C_4$-alkyl and each of which has 3 to 10 carbon atoms.

R furthermore particularly preferably represents cyclopentyl, cyclohexyl, cycloheptyl, cyclooctyl, cyclononyl, bicyclo[2.2.1]heptyl or bicyclo[2.2.2]octyl.

R furthermore preferably represents unsubstituted $C_2$-$C_{20}$-alkyl or represents $C_1$-$C_{20}$-alkyl which is mono- or polysubstituted by identical or different substituents from the group consisting of fluorine, chlorine, bromine, iodine and/or $C_3$-$C_6$-cycloalkyl, where the cycloalkyl moiety for its part may optionally be mono- to tetrasubstituted by identical or different substituents from the group consisting of fluorine, chlorine, bromine, iodine, $C_1$-$C_4$-alkyl and $C_1$-$C_4$-haloalkyl.

R furthermore particularly preferably represents unsubstituted $C_2$-$C_{20}$-alkyl.

R furthermore particularly preferably represents $C_1$-$C_{20}$-alkyl which is substituted by chlorine, cyclopropyl, dichlorocyclopropyl, cyclobutyl, cyclopentyl or cyclohexyl.

$R^{12}$ preferably represents hydrogen, cyano, fluorine, chlorine, bromine, iodine, methyl, ethyl, isopropyl, methoxy, ethoxy, methylthio, ethylthio, cyclopropyl, $C_1$-$C_2$-haloalkyl, $C_1$-$C_2$-haloalkoxy having in each case 1 to 5 fluorine, chlorine and/or bromine atoms, trifluoromethylthio, difluoromethylthio, aminocarbonyl, aminocarbonylmethyl or aminocarbonylethyl.

$R^{12}$ particularly preferably represents hydrogen, fluorine, chlorine, bromine, iodine, methyl, ethyl, isopropyl, monofluoromethyl, monofluoroethyl, difluoromethyl, trifluoromethyl, difluorochloromethyl, trichloromethyl, dichloromethyl, cyclopropyl, methoxy, ethoxy, trifluoromethoxy, trichloromethoxy, methylthio, ethylthio, trifluoromethylthio or difluoromethylthio.

$R^{12}$ very particularly preferably represents hydrogen, fluorine, chlorine, bromine, iodine, methyl, isopropyl, monofluoromethyl, monofluoroethyl, difluoromethyl, trifluoromethyl, difluorochloromethyl or trichloromethyl.

$R^{12}$ especially preferably represents methyl, difluoromethyl, trifluoromethyl or 1-fluoroethyl.

$R^{13}$ preferably represents hydrogen, fluorine, chlorine, bromine, iodine, methyl, ethyl, methoxy, ethoxy, methylthio or ethylthio.

$R^{13}$ particularly preferably represents hydrogen, fluorine, chlorine, bromine, iodine or methyl.

$R^{13}$ very particularly preferably represents hydrogen, fluorine, chlorine or methyl.

$R^{14}$ preferably represents hydrogen, methyl, ethyl, n-propyl, isopropyl, $C_1$-$C_2$-haloalkyl having 1 to 5 fluorine, chlorine and/or bromine atoms, hydroxymethyl, hydroxyethyl, cyclopropyl, cyclopentyl, cyclohexyl or phenyl.

$R^{14}$ particularly preferably represents hydrogen, methyl, ethyl, isopropyl, trifluoromethyl, difluoromethyl, hydroxymethyl, hydroxyethyl or phenyl.

$R^{14}$ very particularly preferably represents hydrogen, methyl, trifluoromethyl or phenyl.

$R^{14}$ especially preferably represents methyl.

$R^{15}$ and $R^{16}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{15}$ and $R^{16}$ independently of one another particularly preferably represent hydrogen, fluorine, chlorine, bromine, methyl, ethyl, difluoromethyl, trifluoromethyl, difluorochloromethyl or trichloromethyl.

$R^{15}$ and $R^{16}$ independently of one another very particularly preferably represent hydrogen, fluorine, chlorine, bromine, methyl, ethyl, difluoromethyl, trifluoromethyl or trichloromethyl.

$R^{15}$ and $R^{16}$ especially each represent hydrogen.

$R^{17}$ preferably represents fluorine, chlorine, bromine, cyano, methyl, ethyl, $C_1$-$C_2$-haloalkyl or $C_1$-$C_2$-haloalkoxy having in each case 1 to 5 fluorine, chlorine and/or bromine atoms.

$R^{17}$ particularly preferably represents fluorine, chlorine, bromine, cyano, methyl, trifluoromethyl, trifluoromethoxy, difluoromethoxy, difluorochloromethoxy or trichloromethoxy.

$R^{17}$ very particularly preferably represents fluorine, chlorine, bromine, iodine, methyl, trifluoromethyl or trifluoromethoxy.

$R^{17}$ especially preferably represents methyl.

$R^{17}$ especially preferably represents trifluoromethyl.

$R^{18}$ and $R^{19}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{18}$ and $R^{19}$ independently of one another particularly preferably represent hydrogen, fluorine, chlorine, bromine, methyl, ethyl, difluoromethyl, trifluoromethyl, difluorochloromethyl or trichloromethyl.

$R^{18}$ and $R^{19}$ independently of one another very particularly preferably represent hydrogen, fluorine, chlorine, bromine, methyl, ethyl, difluoromethyl, trifluoromethyl or trichloromethyl.

$R^{18}$ and $R^{19}$ especially preferably each represent hydrogen.

$R^{20}$ preferably represents hydrogen, fluorine, chlorine, bromine, methyl, ethyl or $C_1$-$C_2$-haloalkyl having 1 to 5 fluorine, chlorine and/or bromine atoms.

$R^{20}$ particularly preferably represents hydrogen, fluorine, chlorine, bromine, iodine, methyl or trifluoromethyl.

$R^{20}$ very particularly preferably represents methyl.

$R^{20}$ especially preferably represents trifluoromethyl.

$R^{21}$ preferably represents hydrogen, fluorine, chlorine, bromine, iodine, hydroxyl, cyano, $C_1$-$C_4$-alkyl, $C_1$-$C_2$-haloalkyl, $C_1$-$C_2$-haloalkoxy or $C_1$-$C_2$-haloalkylthio having in each case 1 to 5 fluorine, chlorine and/or bromine atoms.

$R^{21}$ particularly preferably represents hydrogen, fluorine, chlorine, bromine, iodine, hydroxyl, cyano, methyl, ethyl, n-propyl, isopropyl, n-butyl, isobutyl, sec-butyl, tert-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio.

$R^{21}$ very particularly preferably represents hydrogen, fluorine, chlorine, bromine, iodine, methyl, difluoromethyl, trifluoromethyl or trichloromethyl.

$R^{21}$ especially preferably represents iodine, methyl, difluoromethyl or trifluoromethyl.

$R^{22}$ preferably represents fluorine, chlorine, bromine, iodine, hydroxyl, cyano, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{22}$ particularly preferably represents fluorine, chlorine, bromine, iodine, hydroxyl, cyano, methyl, ethyl, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy.

$R^{22}$ very particularly preferably represents fluorine, chlorine, bromine, iodine, methyl, trifluoromethyl, difluoromethyl or trichloromethyl.

$R^{23}$ preferably represents hydrogen, fluorine, chlorine, bromine, iodine, cyano, $C_1$-$C_4$-alkyl, methoxy, ethoxy, methylthio, ethylthio, $C_1$-$C_2$-haloalkyl or $C_1$-$C_2$-haloalkoxy having in each case 1 to 5 fluorine, chlorine and/or bromine atoms, $C_1$-$C_2$-alkylsulphinyl or $C_1$-$C_2$-alkylsulphonyl.

$R^{23}$ particularly preferably represents hydrogen, fluorine, chlorine, bromine, iodine, cyano, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy, trichloromethoxy, methylsulphinyl or methylsulphonyl.

$R^{23}$ very particularly preferably represents hydrogen, fluorine, chlorine, bromine, iodine, n-propyl, isopropyl, n-butyl, isobutyl, sec-butyl, tert-butyl, trifluoromethyl, difluoromethyl, trichloromethyl, methylsulphinyl or methylsulphonyl.

$R^{23}$ especially preferably represents hydrogen.

$R^{24}$ preferably represents methyl, ethyl or $C_1$-$C_2$-haloalkyl having 1 to 5 fluorine, chlorine and/or bromine atoms.

$R^{24}$ particularly preferably represents methyl, ethyl, trifluoromethyl, difluoromethyl, difluorochloromethyl or trichloromethyl.

$R^{25}$ preferably represents methyl or ethyl.

$R^{25}$ particularly preferably represents methyl.

$Q^1$ preferably represents S (sulphur), $SO_2$ or $CH_2$.

$Q^1$ particularly preferably represents S (sulphur) or $CH_2$.

$Q^1$ very particularly preferably represents S (sulphur).

p preferably represents 0 or 1.

p particularly preferably represents 0.

$R^{26}$ preferably represents methyl, ethyl or $C_1$-$C_2$-haloalkyl having 1 to 5 fluorine, chlorine and/or bromine atoms.

$R^{26}$ particularly preferably represents methyl, ethyl, trifluoromethyl, difluoromethyl, difluorochloromethyl or trichloromethyl.

$R^{26}$ very particularly preferably represents methyl, trifluoromethyl, difluoromethyl or trichloromethyl.

$R^{27}$ preferably represents methyl, ethyl or $C_1$-$C_2$-haloalkyl having 1 to 5 fluorine, chlorine and/or bromine atoms.

$R^{27}$ particularly preferably represents methyl, ethyl, trifluoromethyl, difluoromethyl, difluorochloromethyl or trichloromethyl.

$R^{27}$ very particularly preferably represents methyl, trifluoromethyl, difluoromethyl or trichloromethyl.

$R^{28}$ and $R^{29}$ independently of one another preferably represent hydrogen, fluorine, chlorine, bromine, amino, methyl, ethyl or $C_1$-$C_2$-haloalkyl having 1 to 5 fluorine, chlorine and/or bromine atoms.

$R^{28}$ and $R^{29}$ independently of one another particularly preferably represent hydrogen, fluorine, chlorine, bromine, methyl, ethyl, trifluoromethyl, difluoromethyl, difluorochloromethyl or trichloromethyl.

$R^{28}$ and $R^{29}$ independently of one another very particularly preferably represent hydrogen, fluorine, chlorine, bromine, methyl, trifluoromethyl, difluoromethyl or trichloromethyl.

$R^{28}$ and $R^{29}$ especially preferably each represent hydrogen.

$R^{30}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{30}$ particularly preferably represents hydrogen, fluorine, chlorine, bromine, iodine, methyl, ethyl, trifluoromethyl, difluoromethyl, difluorochloromethyl or trichloromethyl.

$R^{30}$ very particularly preferably represents hydrogen, fluorine, chlorine, bromine, iodine, methyl, trifluoromethyl, difluoromethyl or trichloromethyl.

$R^{30}$ especially preferably represents methyl.

$R^{31}$ and $R^{32}$ independently of one another preferably represent hydrogen, fluorine, chlorine, bromine, amino, nitro, methyl, ethyl or $C_1$-$C_2$-haloalkyl having 1 to 5 fluorine, chlorine and/or bromine atoms.

$R^{31}$ and $R^{32}$ independently of one another particularly preferably represent hydrogen, fluorine, chlorine, bromine, nitro, methyl, ethyl, trifluoromethyl, difluoromethyl, difluorochloromethyl or trichloromethyl.

$R^{31}$ and $R^{32}$ independently of one another very particularly preferably represent hydrogen, fluorine, chlorine, bromine, methyl, trifluoromethyl, difluoromethyl or trichloromethyl.

$R^{31}$ and $R^{32}$ especially preferably each represent hydrogen.

$R^{33}$ preferably represents hydrogen, fluorine, chlorine, bromine, methyl, ethyl or $C_1$-$C_2$-haloalkyl having 1 to 5 fluorine, chlorine and/or bromine atoms.

$R^{33}$ particularly preferably represents hydrogen, fluorine, chlorine, bromine, methyl, ethyl, trifluoromethyl, difluoromethyl, difluorochloromethyl or trichloromethyl.

$R^{33}$ very particularly preferably represents hydrogen, fluorine, chlorine, bromine, methyl, trifluoromethyl, difluoromethyl or trichloromethyl.

$R^{33}$ especially preferably represents methyl.

$R^{34}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{34}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{34}$ very particularly preferably represents hydrogen, fluorine, chlorine, bromine, amino, methylamino, dimethylamino, methyl, trifluoromethyl, difluoromethyl or trichloromethyl.

$R^{34}$ especially preferably represents amino, methylamino, dimethylamino, methyl or trifluoromethyl.

$R^{35}$ preferably represents fluorine, chlorine, bromine, methyl, ethyl or $C_1$-$C_2$-haloalkyl having 1 to 5 fluorine, chlorine and/or bromine atoms.

$R^{35}$ particularly preferably represents fluorine, chlorine, bromine, methyl, ethyl, trifluoromethyl, difluoromethyl, difluorochloromethyl or trichloromethyl.

$R^{35}$ very particularly preferably represents fluorine, chlorine, bromine, methyl, trifluoromethyl, difluoromethyl or trichloromethyl.

$R^{35}$ especially preferably represents methyl, trifluoromethyl or difluoromethyl.

$R^{36}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{36}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{36}$ very particularly preferably represents hydrogen, fluorine, chlorine, bromine, amino, methylamino, dimethylamino, methyl, trifluoromethyl, difluoromethyl or trichloromethyl.

$R^{36}$ ally represents amino, methylamino, dimethylamino, methyl or trifluoromethyl.

$R^{37}$ preferably represents fluorine, chlorine, bromine, methyl, ethyl or $C_1$-$C_2$-haloalkyl having 1 to 5 fluorine, chlorine and/or bromine atoms.

$R^{37}$ particularly preferably represents fluorine, chlorine, bromine, methyl, ethyl, trifluoromethyl, difluoromethyl, difluorochloromethyl or trichloromethyl.

$R^{37}$ very particularly preferably represents fluorine, chlorine, bromine, methyl, trifluoromethyl, difluoromethyl or trichloromethyl.

$R^{37}$ especially preferably represents methyl, trifluoromethyl or difluoromethyl.

$R^{38}$ preferably represents fluorine, chlorine, bromine, methyl, ethyl or $C_1$-$C_2$-haloalkyl having 1 to 5 fluorine, chlorine and/or bromine atoms.

$R^{38}$ particularly preferably represents fluorine, chlorine, bromine, methyl, ethyl, trifluoromethyl, difluoromethyl, difluorochloromethyl or trichloromethyl.

$R^{38}$ very particularly preferably represents fluorine, chlorine, bromine, methyl, trifluoromethyl, difluoromethyl or trichloromethyl.

$R^{39}$ preferably represents hydrogen, methyl or ethyl.

$R^{39}$ particularly preferably represents methyl.

$R^{40}$ preferably represents fluorine, chlorine, bromine, methyl or ethyl.

$R^{40}$ particularly preferably represents fluorine, chlorine or methyl.

$R^{41}$ preferably represents methyl, ethyl or $C_1$-$C_2$-haloalkyl having 1 to 5 fluorine, chlorine and/or bromine atoms.

$R^{41}$ particularly preferably represents methyl, ethyl, trifluoromethyl, difluoromethyl, difluorochloromethyl or trichloromethyl.

$R^{41}$ very particularly preferably represents methyl, trifluoromethyl, difluoromethyl or trichloromethyl.

$R^{41}$ especially preferably represents methyl or trifluoromethyl.

$R^{42}$ preferably represents hydrogen, fluorine, chlorine, bromine, methyl, ethyl or $C_1$-$C_2$-haloalkyl having 1 to 5 fluorine, chlorine and/or bromine atoms.

$R^{42}$ particularly preferably represents hydrogen, fluorine, chlorine, bromine, methyl or trifluoromethyl.

$R^{43}$ preferably represents fluorine, chlorine, bromine, iodine, hydroxyl, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

R⁴³ particularly preferably represents fluorine, chlorine, bromine, iodine, methyl, ethyl, n-propyl, isopropyl, n-butyl, isobutyl, sec-butyl, tert-butyl, trifluoromethyl, difluoromethyl, difluorochloromethyl or trichloromethyl.

R⁴³ very particularly preferably represents fluorine, chlorine, bromine, iodine, methyl, trifluoromethyl, difluoromethyl or trichloromethyl.

R⁴⁴ preferably represents hydrogen, methyl, ethyl, $C_1$-$C_2$-haloalkyl having 1 to 5 fluorine, chlorine and/or bromine atoms, $C_1$-$C_2$-alkoxy-$C_1$-$C_2$-alkyl, hydroxymethyl, hydroxyethyl, methylsulphonyl or dimethylaminosulphonyl.

R⁴⁴ particularly preferably represents hydrogen, methyl, ethyl, trifluoromethyl, methoxymethyl, ethoxymethyl, hydroxymethyl or hydroxyethyl.

R⁴⁴ very particularly preferably represents methyl or methoxymethyl.

R⁴⁵ preferably represents hydrogen, fluorine, chlorine, bromine, methyl, ethyl or $C_1$-$C_2$-haloalkyl having 1 to 5 fluorine, chlorine and/or bromine atoms.

R⁴⁵ particularly preferable represents hydrogen, fluorine, chlorine, bromine, methyl, ethyl, trifluoromethyl, difluoromethyl or trichloromethyl.

R⁴⁵ very particularly preferably represents hydrogen or methyl.

R⁴⁶ preferably represents hydrogen, fluorine, chlorine, bromine, iodine, cyano, methyl, ethyl, isopropyl or $C_1$-$C_2$-haloalkyl having 1 to 5 fluorine, chlorine and/or bromine atoms.

R⁴⁶ particularly preferably represents hydrogen, fluorine, chlorine, bromine, cyano, methyl, ethyl, isopropyl, trifluoromethyl, difluoromethyl, difluorochloromethyl or trichloromethyl.

R⁴⁶ very particularly preferably represents hydrogen, methyl, difluoromethyl or trifluoromethyl.

R⁴⁷ preferably represents hydrogen, fluorine, chlorine, bromine, methyl, ethyl or $C_1$-$C_2$-haloalkyl having 1 to 5 fluorine, chlorine and/or bromine atoms.

R⁴⁷ particularly preferably represents hydrogen, fluorine, chlorine, bromine, iodine, methyl or trifluoromethyl.

R⁴⁷ very particularly preferably represents hydrogen.

R⁴⁸ preferably represents methyl, ethyl, n-propyl or isopropyl.

R⁴⁸ particularly preferably represents methyl or ethyl.

Preference is given to those compounds of the formula (I) in which all radicals each have the preferred meanings mentioned above.

Particular preference is given to those compounds of the formula (I) in which all radicals each have the particularly preferred meanings mentioned above.

Compounds of the formula (I) which are emphasized are those mentioned below:

(1) N-[2-(1,3-dimethylbutyl)phenyl]-1,3-dimethyl-1H-pyrazole-4-carboxamide (known from JP-A 10-251240) of the formula

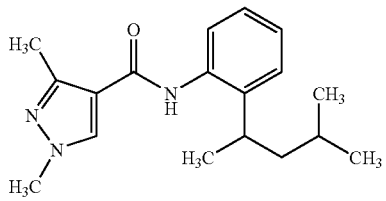 [SMILES: Cc1nn(C)cc1C(=O)Nc1ccccc1C(C)CC(C)C]

(2) N-[2-(1,3-dimethylbutyl)phenyl]-5-fluoro-1,3-dimethyl-1H-pyrazole-4-carboxamide (known from WO 03/010149) of the formula

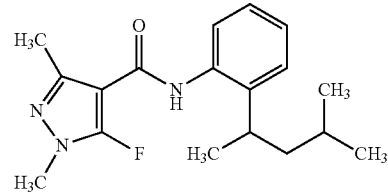

(3) N-[2-(1,3-dimethylbutyl)phenyl]-5-chloro-1,3-dimethyl-1H-pyrazole-4-carboxamide (known from JP-A 10-251240) of the formula

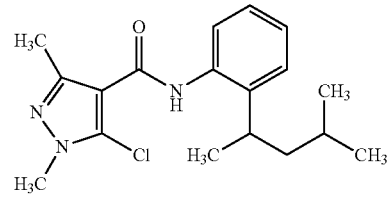

(4) 3-(difluoromethyl)-N-[2-(1,3-dimethylbutyl)phenyl]-1-methyl-1H-pyrazole-4-carboxamide of the formula

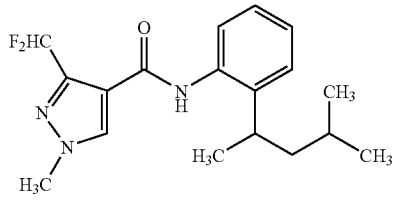 [SMILES: CC(C)CC(C)c1ccccc1NC(=O)c1cn(C)nc1C(F)F]

(5) 3-(trifluoromethyl)-N-[2-(1,3-dimethylbutyl)phenyl]-5-fluoro-1-methyl-1H-pyrazole-4-carboxamide (known from WO 2004/067515) of the formula

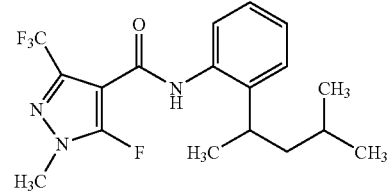 [SMILES: CC(C)CC(C)c1ccccc1NC(=O)c1c(C(F)(F)F)nn(C)c1F]

(6) 3-(trifluoromethyl)-N-[2-(1,3-dimethylbutyl)phenyl]-5-chloro-1-methyl-1H-pyrazole-4-carboxamide (known from JP-A 10-251240) of the formula

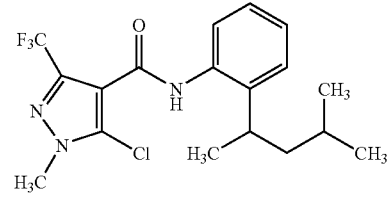

(7) 1,3-dimethyl-N-[2-(1,3,3-trimethylbutyl)phenyl]-1H-pyrazole-4-carboxamide of the formula

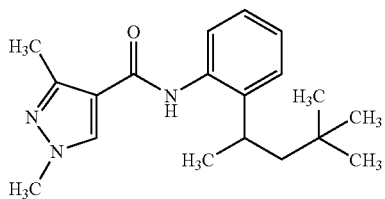 [SMILES: Cc1nn(C)cc1C(=O)Nc1ccccc1C(C)CC(C)(C)C]

(8) 5-fluoro-1,3-dimethyl-N-[2-(1,3,3-trimethylbutyl)phenyl]-1H-pyrazole-4-carboxamide (known from WO 03/010149) of the formula

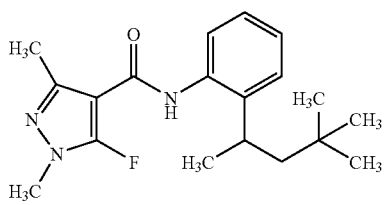 [SMILES: Cc1nn(C)c(F)c1C(=O)Nc1ccccc1C(C)CC(C)(C)C]

(9) 3-(difluoromethyl)-1-methyl-N-[2-(1,3,3-trimethylbutyl)phenyl]-1H-pyrazole-4-carboxamide of the formula

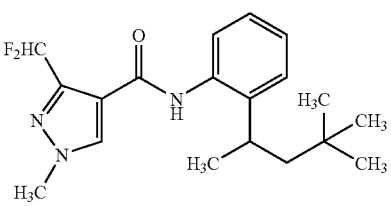 [SMILES: CC(CC(C)(C)C)c1ccccc1NC(=O)c1cn(C)nc1C(F)F]

(10) 3-(trifluoromethyl)-1-methyl-N-[2-(1,3,3-trimethylbutyl)phenyl]-1H-pyrazole-4-carboxamide of the formula

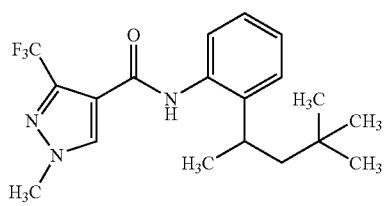

(11) 3-(trifluoromethyl)-5-fluoro-1-methyl-N-[2-(1,3,3-trimethylbutyl)phenyl]-1H-pyrazole-4-carboxamide (known from WO 2004/067515) of the formula

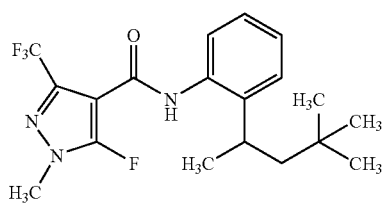

(12) 3-(trifluoromethyl)-5-chloro-1-methyl-N-[2-(1,3,3-trimethylbutyl)phenyl]-1H-pyrazole-4-carboxamide of the formula

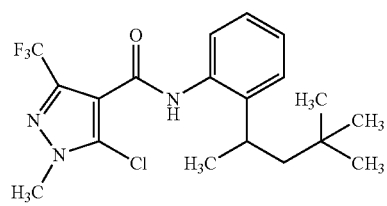

(13) N-[2-(1,3-dimethylbutyl)phenyl]-2-iodobenzamide (known from WO 2004/005242) of the formula

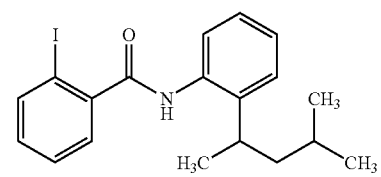 [SMILES: CC(C)CC(C)c1ccccc1NC(=O)c1ccccc1I]

(14) 2-iodo-N-[2-(1,3,3-trimethylbutyl)phenyl]benzamide (known from WO 2004/005242) of the formula

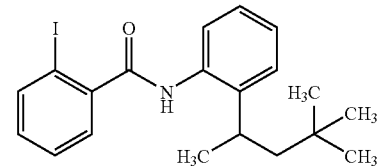 [SMILES: CC(CC(C)(C)C)c1ccccc1NC(=O)c1ccccc1I]

(15) N-[2-(1,3-dimethylbutyl)phenyl]-2-(trifluoromethyl)benzamide (known from WO 2004/005242) of the formula

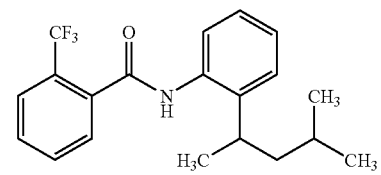

(16) 2-(trifluoromethyl)-N-[2-(1,3,3-trimethylbutyl)phenyl]benzamide (known from WO 2004/005242) of the formula

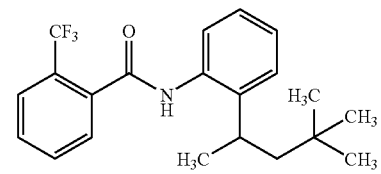 [SMILES: CC(CC(C)(C)C)c1ccccc1NC(=O)c1ccccc1C(F)(F)F]

(17) boscalid (known from DE-A 195 31 813) of the formula

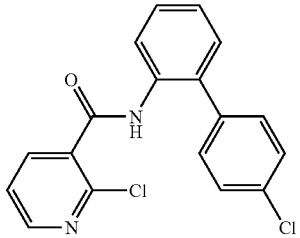 [SMILES: O=C(Nc1ccccc1-c1ccc(Cl)cc1)c1cccnc1Cl]

(18) N-(3-p-tolylthiophen-2-yl)-1-methyl-3-trifluoromethyl-1H-pyrazole-4-carboxamide (known from EP-A 0 737 682) of the formula

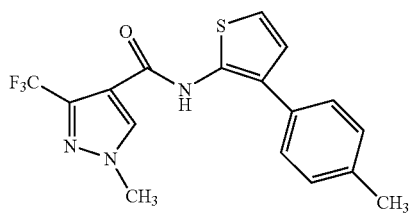 [SMILES: Cc1ccc(-c2ccsc2NC(=O)c2cn(C)nc2C(F)(F)F)cc1]

(19) penthiopyrad (known from EP-A 0 737 682) of the formula

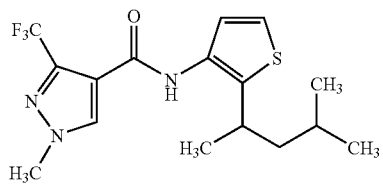 [SMILES: CC(C)CC(C)c1sccc1NC(=O)c1cn(C)nc1C(F)(F)F]

(20) N-[2-(1,3-dimethylbutyl)phenyl]-methyl-4-(trifluoromethyl)-1H-pyrrole-3-carboxamide (known from WO 02/38542) of the formula

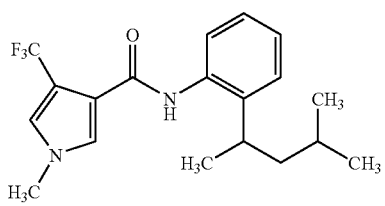

(21) N-(3',4'-dichloro-5-fluoro-1,1'-biphenyl-2-yl)-3-(difluoromethyl)-1-methyl-1H-pyrazole-4-carboxamide (known from WO 03/070705) of the formula

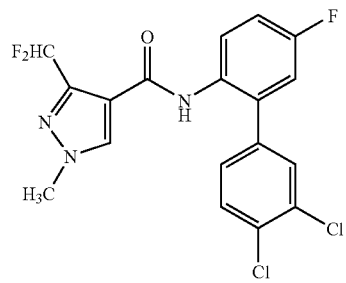 [SMILES: Cn1cc(C(=O)Nc2ccc(F)cc2-c2ccc(Cl)c(Cl)c2)c(C(F)F)n1]

(22) 3-(difluoromethyl)-N-{3'-fluoro-4'-[(E)-(methoxyimino)methyl]-1,1'-biphenyl-2-yl}-1-methyl-1H-pyrazole-4-carboxamide (known from WO 02/08197) of the formula

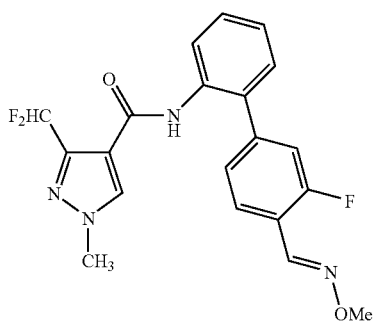 [SMILES: CO/N=C/c1ccc(-c2ccccc2NC(=O)c2cn(C)nc2C(F)F)cc1F]

(23) 3-(trifluoromethyl)-N-{3'-fluoro-4'-[(E)-(methoxyimino)methyl]-1,1'-biphenyl-2-yl}-1-methyl-1H-pyrazole-4-carboxamide (known from WO 02/08197) of the formula

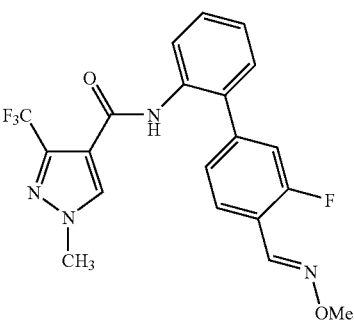 [SMILES: CO/N=C/c1ccc(-c2ccccc2NC(=O)c2cn(C)nc2C(F)(F)F)cc1F]

(24) N-(3',4'-dichloro-1,1'-biphenyl-2-yl)-5-fluoro-1,3-dimethyl-1H-pyrazole-4-carboxamide (known from WO 00/14701) of the formula

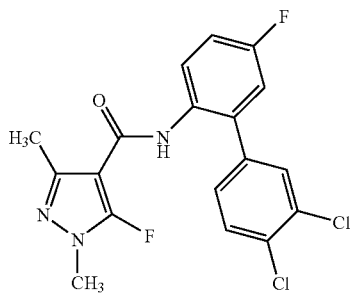 [SMILES: Cc1nn(C)c(F)c1C(=O)Nc1ccc(F)cc1-c1ccc(Cl)c(Cl)c1]

(25) N-(4'-chloro-3'-fluoro-1,1'-biphenyl-2-yl)-2-methyl-4-(trifluoromethyl)-1,3-thiazole-5-carboxamide (known from WO 03/066609) of the formula

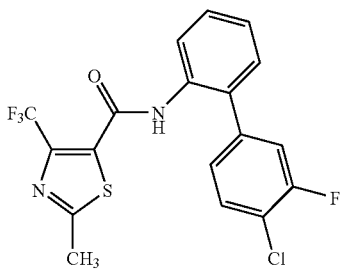 [SMILES: Cc1nc(C(F)(F)F)c(C(=O)Nc2ccccc2-c2ccc(Cl)c(F)c2)s1]

(26) N-(4'-chloro-1,1'-biphenyl-2-yl)-4-(difluoromethyl)-2-methyl-1,3-thiazole-5-carboxamide (known from WO 03/066610) of the formula

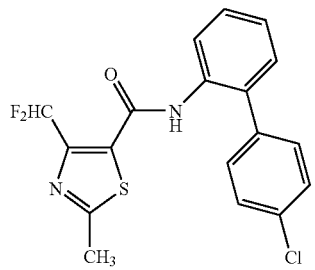 [SMILES: Cc1nc(C(F)F)c(C(=O)Nc2ccccc2-c2ccc(Cl)cc2)s1]

(27) N-(4'-bromo-1,1'-biphenyl-2-yl)-4-(difluoromethyl)-2-methyl-1,3-thiazole-5-carboxamide (known from WO 03/066610) of the formula

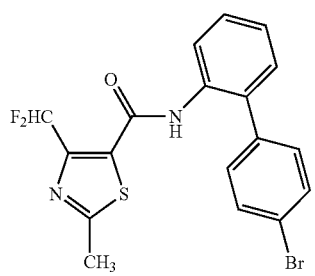 [SMILES: Cc1nc(C(F)F)c(C(=O)Nc2ccccc2-c2ccc(Br)cc2)s1]

(28) 4-(difluoromethyl)-2-methyl-N-[4'-(trifluoromethyl)-1,1'-biphenyl-2-yl]-1,3-thiazole-5-carboxamide (known from WO 03/066610) of the formula

(29) N-(4'-iodo-1,1'-biphenyl-2-yl)-4-(difluoromethyl)-2-methyl-1,3-thiazole-5-carboxamide (known from WO 03/066610) of the formula

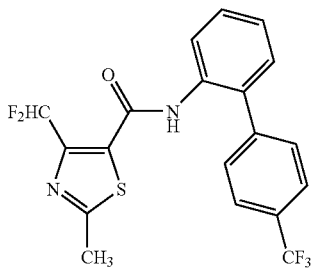 [SMILES: Cc1nc(C(F)F)c(C(=O)Nc2ccccc2-c2ccc(C(F)(F)F)cc2)s1]

(30) N-(4'-chloro-3'-fluoro-1,1'-biphenyl-2-yl)-4-(difluoromethyl)-1,3-thiazole-5-carboxamide (known from WO 03/066610) of the formula

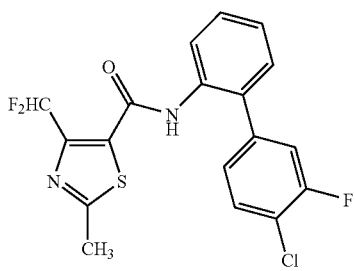 [SMILES: Cc1nc(C(F)F)c(C(=O)Nc2ccccc2-c2ccc(Cl)c(F)c2)s1]

(31) tiadinil (known from U.S. Pat. No. 6,616,054) of the formula

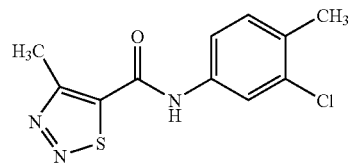 [SMILES: Cc1ccc(NC(=O)c2snnc2C)cc1Cl]

(32) N-[2-(1,3-dimethylbutyl)phenyl]-1-methyl-4-(trifluoromethyl)-1H-pyrrole-3-carboxamide (known from WO 02/38542) of the formula

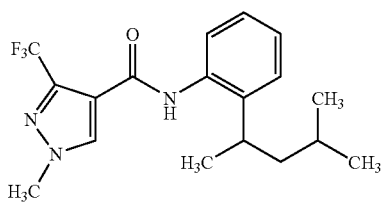 [SMILES: CC(C)CC(C)c1ccccc1NC(=O)c1cn(C)nc1C(F)(F)F]

(33) N-(4'-chlorobiphenyl-2-yl)-3-iodo-1-methyl-1H-pyrazole-4-carboxamide (known from WO 2004/103975) of the formula

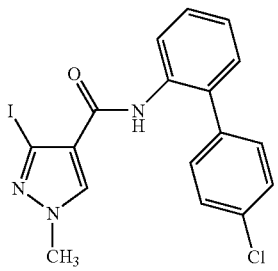 [SMILES: Cn1cc(C(=O)Nc2ccccc2-c2ccc(Cl)cc2)c(I)n1]

(34) 4-(difluoromethyl)-N-[3'-fluoro-4'-(trifluoromethyl)biphenyl-2-yl]-2-methyl-1,3-thiazole-5-carboxamide (known from WO 03/066610) of the formula

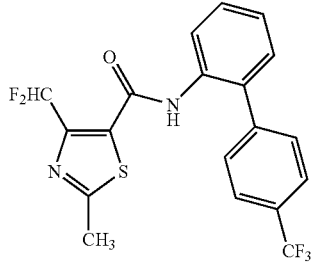 [SMILES: Cc1nc(C(F)F)c(C(=O)Nc2ccccc2-c2ccc(C(F)(F)F)cc2)s1]

(35) 3-(difluoromethyl)-N-[2-(3,3-dimethylbutyl)phenyl]-1-methyl-1H-pyrazole-4-carboxamide (known from WO 2005/042494) of the formula

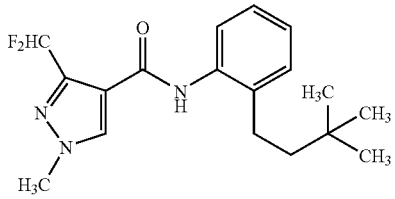 [SMILES: Cn1cc(C(=O)Nc2ccccc2CCC(C)(C)C)c(C(F)F)n1]

(36) N-[2-(3,3-dimethylbutyl)phenyl]-5-fluoro-1,3-dimethyl-1H-pyrazole-4-carboxamide (known from WO 2005/042494) of the formula

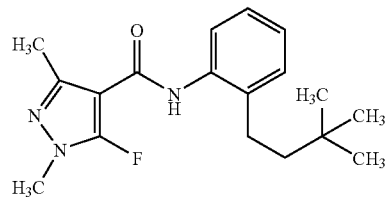 [SMILES: Cc1nn(C)c(F)c1C(=O)Nc1ccccc1CCC(C)(C)C]

(37) N-[3'-fluoro-4'-(trifluoromethyl)biphenyl-2-yl]-3-iodo-1-methyl-1H-pyrazole-4-carboxamide (known from WO 2004/103975) of the formula

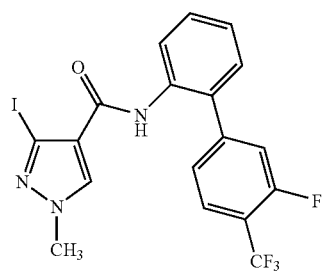 [SMILES: Cn1cc(C(=O)Nc2ccccc2-c2ccc(C(F)(F)F)c(F)c2)c(I)n1]

(38) 3-(difluoromethyl)-N-[2-(1,3-dimethylbutyl)-4-fluorophenyl]-1-methyl-1H-pyrazole-4-carboxamide (known from WO 2005/042492) of the formula

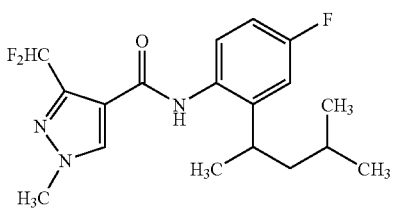 [SMILES: CC(C)CC(C)c1cc(F)ccc1NC(=O)c1cn(C)nc1C(F)F]

(39) 4-(difluoromethyl)-2-methyl-N-[2-[2-(trimethylsilyl)ethyl]-3-thienyl]-1,3-thiazole-5-carboxamide

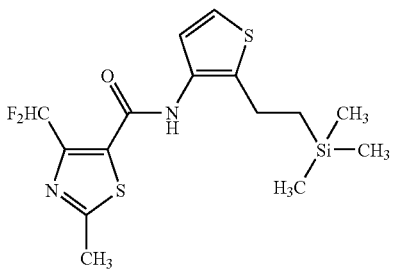 [SMILES: Cc1nc(C(F)F)c(C(=O)Nc2ccsc2CC[Si](C)(C)C)s1]

Emphasis is given to compounds of the formula (I) in which $R^1$ represents hydrogen.

Emphasis is given to compounds of the formula (I) in which $R^1$ represents formyl.

Emphasis is furthermore given to compounds of the formula (I) in which $R^1$ represents —C(=O)C(=O)$R^2$, where $R^2$ is as defined above.

The definition $C_1$-$C_{20}$-alkyl comprises the largest range defined here for an alkyl radical. Specifically, this definition comprises the meanings methyl, ethyl, n-, isopropyl, n-, iso-, sec-, tert-butyl, and in each case all isomeric pentyls, hexyls, heptyls, octyls, nonyls, decyls, undecyls, dodecyls, tridecyls, tetradecyls, pentadecyls, hexadecyls, heptadecyls, octadecyls, nonadecyls and eicosyls. Among these, pre-ference is given to the meanings methyl, ethyl, n-, isopropyl, n-, iso-, sec-, tert-butyl, n-pentyl, 1-methylbutyl, 2-methylbutyl, 3-methylbutyl, 1,2-dimethylpropyl, 2,2-dimethylpropyl, n-hexyl, 1-methylpentyl, 4-methylpentyl, 1,3-dimethylbutyl, 3,3-dimethylbutyl, 1,2,2-trimethylpropyl, n-heptyl, 1-methylhexyl, 5-methylhexyl, 1,4-dimethylpentyl, 4,4-dimethylpentyl, 1,3,3-trimethylbutyl, 1,2,3-trimethylbutyl.

Saturated or unsaturated hydrocarbon radicals, such as alkyl or alkenyl, can in each case be straight-chain or branched as far as this is possible, including in combination with heteroatoms, such as, for example, in alkoxy. Doubly attached hydrocarbon radicals, such as alkylene (alkanediyl), can also in each case be straight-chain or branched as far as this is possible.

Optionally substituted radicals can be mono- or polysubstituted, where in the case of polysubstitutions the substituents can be identical or different. Thus, the definition dialkylamino also includes an amino group which is substituted asymmetrically by alkyl, such as, for example, methylethylamino.

Halogen-substituted radicals, such as, for example, haloalkyl, are mono- or polyhalogenated. In the case of polyhalogenation, the halogen atoms can be identical or different. Here, halogen represents fluorine, chlorine, bromine and iodine, in particular fluorine, chlorine and bromine.

The general or preferred radical definitions or illustrations given above can be combined between the respective ranges and preferred ranges as desired. The definitions apply both to the end products and, correspondingly, to precursors and intermediates.

The compounds according to the invention have strong microbicidal action and can be used for controlling certain rust fungi, such as soya bean rust and coffee rust, in crop protection.

The following diseases of soya plants can preferably be controlled:
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*), black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*). Particular preference is given to using the carboxamides of the formula (I) for controlling *Phakopsora pachyrhizi*.

In the present case, unwanted microorganisms are to be understood as meaning the organisms mentioned above. The compounds according to the invention can therefore be employed for protecting plants against attack by the above-mentioned pathogens within a certain period of time after the treatment. The period of time within which protection is effected generally extends from 1 to 10 days, preferably from 1 to 7 days, after the treatment of the plants with the active compounds.

The fact that the active compounds, in the concentrations required for controlling plant diseases, are well tolerated by plants permits the treatment of above-ground parts of plants, of vegetative propagation material and seed, and of the soil.

In this context, the carboxamides of the formula (I) can be used with particularly good results for controlling soya bean diseases, such as, for example, against Phakopsora species.

The carboxamides of the formula (I) are also suitable for increasing the yield. Moreover, they display a low degree of toxicity and are tolerated well by plants.

All plants and plant parts can be treated in accordance with the invention. Plants are understood as meaning, in the present context, all plants and plant populations, such as desired and undesired wild plants or crop plants (including naturally occurring crop plants). Crop plants may be plants which can be obtained by conventional breeding and optimization methods or else by biotechnological and genetic engineering methods or by combinations of these methods, including the transgenic plants and including the plant varieties capable or not capable of being protected by plant breeders' rights. Plant parts are to be understood as meaning all above-ground and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include harvested material and vegetative and generative propagation material, for example cuttings, tubers, rhizomes, slips and seeds.

The treatment according to the invention with the active compounds, of the plants and plant parts, is carried out directly or by acting on their environment, habitat, or store by the customary treatment methods, for example by immersion, spraying, vaporizing, fogging, broadcasting, painting on and, in the case of propagation material, in particular in the case of seeds, furthermore by coating with one or more coats.

Depending on their respective physical and/or chemical properties, the active compounds can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is liquid solvents, pressurized liquefied gases and/or solid carriers, optionally with the use of surface-active agents, that is emulsifiers and/or dispersants and/or foam formers. If the extender used is water, it is also possible to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants there are suitable: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The carboxamides of the formula (I), as such or in their formulations, can also be used as a mixture with known fungicides, bactericides, acaricides, nematicides, or insecticides, for example, to broaden the activity spectrum or prevent the development of resistance. In many instances, synergistic effects are obtained, i.e. the activity of the mixture exceeds the activity of the individual components.

Examples of co-components in mixtures are the following compounds:
Fungicides:
2-phenylphenol; 8-hydroxyquinoline sulphate; acibenzolar-5-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; boscalid; bromuconazole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrroInitrin; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulphate; cufraneb; cuprous oxide; mancopper; oxine-copper.

Bactericides:
Bronopol, dichlorophen, nitrapyrin, nickel dimethyl dithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
1. Acetylcholine Esterase (AChE) Inhibitors
1.1 Carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulfan, chloethocarb, coumaphos, cyanofenphos, cyanophos, dimetilan, ethiofencarb, fenobucarb, fenothiocarb, formetanate, furathiocarb, isoprocarb, metamn-sodium, methiocarb, methomyl, metolcarb, oxamyl, pirimicarb, promecarb, propoxur, thiodicarb, thiofanox, triazamate, trimethacarb, XMC, xylylcarb)

1.2 Organophosphates (for example acephate, azamethiphos, azinphos (-methyl, -ethyl), bromophosethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-5-methyl, demeton-5-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)

2. Sodium Channel Modulators/Voltage-Gated Sodium Channel Blockers 2.1 Pyrethroids (for example acrinathrin, allethrin (d-cis-trans, d-trans), beta-cyfluthrin, bifenthrin, bioallethrin, bioallethrin-5-cyclopentyl isomer, bioethanomethrin, biopermethrin, bioresmethrin, chlovaporthrin, cis-cypermethrin, cis-resmethrin, cis-permethrin, clocythrin, cyloprothrin, cyfluthrin, cyhalothrin, cypermethrin (alpha-, beta-, theta-, zeta-), cyphenothrin, DDT, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum))

2.2 Oxadiazines (for Example Indoxacarb)

3. Acetylcholine Receptor Agonists/Antagonists 3.1 Chloronicotinyls/neonicotinoids (for example acetamiprid, clothianidin, dinotefuran, imidacloprid, nitenpyram, nithiazine, thiacloprid, thiamethoxam)

3.2 Nicotine, bensultap, cartap

4. Acetylcholine Receptor Modulators 4.1 Spinosyns (for example spinosad)

5. GABA-Gated Chloride Channel Antagonists 5.1 Cyclodiene organochlorines (for example camphechlor, chlordane, endosulfan, gamma-HCH, HCH, heptachlor, lindane, methoxychlor 5.2 Fiproles (for example acetoprole, ethiprole, fipronil, vaniliprole)

6. Chloride Channel Activators 6.1 Mectins (for example abamectin, avermectin, emamectin, emamectin benzoate, ivermectin, milbemectin, milbemycin)

7. Juvenile Hormone Mimetics (for example diofenolan, epofenonane, fenoxycarb, hydroprene, kinoprene, methoprene, pyriproxifen, triprene)

8. Ecdysone Agonists/Disruptors 8.1 Diacylhydrazines (for example chromafenozide, halofenozide, methoxyfenozide, tebufenozide)

9. Chitin Biosynthesis Inhibitors 9.1 Benzoylureas (for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron)

9.2 Buprofezin 9.3 Cyromazine

10. Inhibitors of Oxidative Phosphorylation, ATP Disruptors 10.1 Diafenthiuron 10.2 Organotins (for example azocyclotin, cyhexatin, fenbutatin oxide)

11. Uncouplers of Oxidative Phosphorylation by Interrupting the H-Proton Gradient 11.1 Pyrroles (for example chlorfenapyr)

11.2 Dinitrophenols (for example binapacyrl, dinobuton, dinocap, DNOC)

12. Site-I Electron Transport Inhibitors 12.1 METIs (for example fenazaquin, fenpyroximate, pyrimidifen, pyridaben, tebufenpyrad, tolfenpyrad)

12.2 Hydramethylnone 12.3 Dicofol

13. Site-II Electron Transport Inhibitors 13.1 Rotenone

14. Site-III Electron Transport Inhibitors 14.1 Acequinocyl, fluacrypyrim

15. Microbial Disruptors of the Insect Gut Membrane *Bacillus thuringiensis* strains 16. Fat Synthesis Inhibitors 16.1 Tetronic acids (for example spirodiclofen, spiromesifen)

16.2 Tetrarnic acids [for example 3-(2,5-dimethylphenyl)-8-methoxy-2-oxo-1-azaspiro[4.5]dec-3-en-4-yl ethyl carbonate (also known as: carbonic acid, 3-(2,5-dimethylphenyl)-8-methoxy-2-oxo-1-azaspiro[4.5]dec-3-en-4-yl ethyl ester, CAS Reg. No.: 382608-10-8) and carbonic acid, cis-3-(2,5-dimethylphenyl)-8-methoxy-2-oxo-1-azaspiro[4.5]dec-3-en-4-yl ethyl ester (CAS Reg. No.: 203313-25-1)]

17. Carboxamides (for example flonicamid)

18. Octopaminergic Agonists (for example amitraz)

19. Inhibitors of Magnesium-Stimulated ATPase (for example propargite)

20. Phthalamides (for example $N^2$-[1,1-dimethyl-2-(methylsulphonyl)ethyl]-3-iodo-N'-[2-methyl-4-[1,2,2,2-tetrafluoro-1-(trifluoromethyl)ethyl]phenyl]-1,2-benzenedicarboxamide (CAS Reg. No.: 272451-65-7)

21. Nereistoxin Analogues (for example thiocyclam hydrogen oxalate, thiosultap-sodium)

22. Biologicals, Hormones or Pheromones (for example azadirachtin, *Bacillus* spec., *Beauveria* spec., codlemone, *Metarrhizium* spec., *Paecilomyces* spec., thuringiensin, *Verticillium* spec.)

23. Active Compounds with Unknown or Unspecific Mechanisms of Action 23.1 Fumigants (for example aluminium phosphide, methyl bromide, sulphuryl fluoride)

23.2 Selective antifeedants (for example cryolite, flonicamid, pymetrozine)

23.3 Mite growth inhibitors (for example clofentezine, etoxazole, hexythiazox)

23.4 Amidoflumet, benclothiaz, benzoximate, bifenazate, bromopropylate, buprofezin, quinomethionate, chlordimeform, chlorobenzilate, chloropicrin, clothiazoben, cycloprene, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin, furthermore the compound 3-methylphenyl propylcarbamate (tsumacide Z), the compound 3-(5-chloro-3-pyridinyl)-8-(2, 2,2-trifluoroethyl)-8-azabicyclo[3.2.1]octane-3-carbonitrile (CAS Reg. No. 185982-80-3) and the corresponding 3-endo isomer (CAS Reg. No. 185984-60-5) (cf. WO 96/37494, WO 98/25923), and preparations which contain insecticidally active plant extracts, nematodes, fungi or viruses.

The active compounds can be employed as such, in the form of their formulations or the use forms prepared therefrom, such as ready-to-use solutions, suspensions, wettable powders, pastes, soluble powders, dusts and granules. They are applied in the customary manner, for example by pouring, spraying, atomizing, broadcasting, dusting, foaming, painting on and the like. It is furthermore possible to apply the active compounds by the ultra-low-volume method, or to inject the active compound preparation or the active compound itself into the soil. The seed of the plants can also be treated.

When employing the carboxamides of the formula (I) as fungicides, the application rates can be varied within a substantial range, depending on the type of application. In the treatment of plant parts, the application rates of active compound are generally between 0.1 and 10 000 g/ha, preferably between 10 and 1000 g/ha. For the treatment of seed, the application rates of active compound are generally between 0.001 and 50 g per kilogram of seed, preferably between 0.01 and 10 g per kilogram of seed. For treating the soil, the application rates of active compound are generally between 0.1 and 10 000 g/ha, preferably between 1 and 5000 g/ha.

As already mentioned above, all plants and their parts can be treated in accordance with the invention. In a preferred embodiment, plant species and plant varieties which are found in the wild or are obtained by traditional biological breeding methods, such as hybridization or protoplast fusion, and parts of the former are treated. In a further preferred embodiment, transgenic plants and plant varieties which have been obtained by recombinant methods, if appropriate in combination with traditional methods (genetically modified organisms), and their parts are treated. The term "parts" or "parts of plants" or "plant parts" has been illustrated above.

Particularly preferably, plants of the plant cultivars which are in each case commercially available or in use are treated according to the invention. Plant cultivars are understood as meaning plants with new properties ("traits") which have been obtained by conventional cultivation, by mutagenesis or else by recombinant DNA techniques. These may be cultivars, breeds, biotypes or genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or extensions of the activity spectrum and/or an increase in the activity of the substances and compositions that can be used according to the invention, better plant growth, increased tolerance to high or low temperatures, increased tolerance to drought or to water or soil salinity, increased flowering performance, easier harvesting, accelerated maturation, higher harvest yields, better quality and/or a higher nutritional value of the harvested products, better storage stability and/or processability of the harvested products which exceed the effects which were actually to be expected are possible.

The preferred transgenic plants or plant cultivars (i.e. those obtained by genetic engineering) which are to be treated according to the invention include all plants which, as a result of the recombinant modification, received genetic material which imparts particularly advantageous useful properties ("traits") to these plants. Examples of such properties are better plant growth, increased tolerance to high or low temperatures, increased tolerance to drought or to water or soil salinity, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes, slugs and snails as the result of toxins formed in the plants, in particular those formed in the plants by the genetic material from Bacillus thuringiensis (for example by the genes CryIA(a), CryIA (b), CryIA(c), CryIIA, CryIIIA, CryIIIB2, Cry9c, Cry2Ab, Cry3Bb and CryIF and also combinations thereof) (hereinbelow referred to as "Bt plants"). Traits which are also particularly emphasized are the increased defence of plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinothricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosates, for example maize, cotton, soya beans), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which cultivars will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The use of the carboxamides of the formula (I) is illustrated by the examples below.

USE EXAMPLES

Example A

Soya Bean Rust Control Test/Spray Application

Preparation of the Test Substances:

5 parts by weight of carboxamide of the formula (I), 142.4 parts by weight of acetone and 7.5 parts by weight of emulsifier (polyoxyethylene alkylphenyl ether) are mixed and adjusted with water to the desired concentration.

Test Method:

Soya beans (cultivar: Enrei) were cultivated in plastic containers having a diameter of 7.5 cm. In each case 3 containers, 6 ml of the test substance (preparation as described above) were sprayed onto the seedlings which had reached the 2.3 leaf stage. One day after spraying, the leaves were inoculated with an urediniospore suspension ($1\times10^5$ urediniospores/ml) of Phakopsora pachyrhizi. 14 days after the inoculation, the degree of infection for each container was evaluated and the efficacy was calculated. The phytotoxicity was also monitored.

TABLE A

| | Soya bean rust control test/spray application | |
|---|---|---|
| Active compound | Active compound application rate in ppm | Efficacy in % |
| (5) | 100 | 80 |
| (33) | 100 | 50 |
| (21) | 250 | 90 |
| | 100 | 50 |
| (2) | 100 | 100 |

TABLE A-continued

Soya bean rust control test/spray application

| Active compound | Active compound application rate in ppm | Efficacy in % |
|---|---|---|
| (34) | 100 | 93 |
| (35) | 100 | 100 |
| (36) | 100 | 100 |
| (37) | 100 | 50 |
| (38) | 100 | 95 |

TABLE A-continued

Soya bean rust control test/spray application

| Active compound | | Active compound application rate in ppm | Efficacy in % |
|---|---|---|---|
| (39) | [chemical structure: thiazole with CH₃ at 2-position, CHF₂ at 4-position, and 5-carboxamide linked to a thiophene bearing a -CH₂CH₂-Si(CH₃)₃ group] | 100 | 80 |

The invention claimed is:

1. A method of controlling *Phakopsora pachyrhizi* rust fungi in soya bean plants comprising treating soya bean plants in need of protection from rust fungi with N-(3',4'-dichloro-5-fluoro-1,1'-biphenyl-2-yl)-3-(difluoromethyl)-1-methyl-1H-pyrazole-4-carboxamide.

2. A method according to claim 1 wherein the soya bean plants are transgenic soya bean plants.

3. A method of controlling *Phakopsora pachyrhizi* rust fungi in soya bean plants according to claim 1 comprising treating a crop in need of protection from rust fungi with (a) N-(3',4'-dichloro-5-fluoro-1,1'-biphenyl-2-yl)-3-(difluoromethyl)-1-methyl-1H-pyrazole-4-carboxamide as the only fungicidally active compound, and (b) optionally, extenders and/or surface-active agents.

4. A method according to claim 3 wherein the soya bean plants are transgenic soya bean plants.

* * * * *